United States Patent
Hehn

(10) Patent No.: US 9,566,137 B2
(45) Date of Patent: Feb. 14, 2017

(54) METHOD FOR VALIDATING A DRILLING TEMPLATE FOR PRODUCING AN IMPLANT-BORNE TOOTH REPLACEMENT

(71) Applicant: Sirona Dental Systems GmbH, Bensheim (DE)

(72) Inventor: Stefan Hehn, Bensheim (DE)

(73) Assignee: SIRONA DENTAL SYSTEMS GmbH, Bensheim (DE)

( * ) Notice: Subject to any disclaimer, the term of this patent is extended or adjusted under 35 U.S.C. 154(b) by 409 days.

(21) Appl. No.: 14/347,548

(22) PCT Filed: Sep. 26, 2012

(86) PCT No.: PCT/EP2012/068900
§ 371 (c)(1),
(2) Date: Mar. 26, 2014

(87) PCT Pub. No.: WO2013/045462
PCT Pub. Date: Apr. 4, 2013

(65) Prior Publication Data
US 2014/0234803 A1 Aug. 21, 2014

(30) Foreign Application Priority Data
Sep. 26, 2011 (DE) .......... 10 2011 083 439

(51) Int. Cl.
*A61C 9/00* (2006.01)
*A61C 13/00* (2006.01)
*A61C 1/08* (2006.01)

(52) U.S. Cl.
CPC .......... *A61C 9/0053* (2013.01); *A61C 1/084* (2013.01); *A61C 13/0004* (2013.01)

(58) Field of Classification Search
CPC .......... A61C 1/08; A61C 13/00; A61C 9/00; A61C 9/0053; A61C 13/0004; A61C 1/084
(Continued)

(56) References Cited

U.S. PATENT DOCUMENTS 6,319,006 B1 11/2001 Scherer et al. .......... 433/215
6,788,986 B1 9/2004 Traber et al.
(Continued)

FOREIGN PATENT DOCUMENTS

EP 0 834 292 A2 4/1998
EP 1 062 916 A2 12/2000
(Continued)

OTHER PUBLICATIONS

International Search Report (ISR) dated Feb. 4, 2013, issued in International Patent Application No. PCT/EP2012/068900, and corresponding English-language translation.
(Continued)

*Primary Examiner* — Nicholas Lucchesi
(74) *Attorney, Agent, or Firm* — Fitzpatrick, Cella, Harper & Scinto

(57) ABSTRACT

The invention relates to a method for validating a drilling template for producing an implant-borne tooth replacement before performing an implant drilling. The drilling template produced is placed on dental structures of a jaw area that is to be provided with the tooth replacement. A measuring element is inserted into the drill guide of the drilling template, wherein the measuring element and at least one partial region of the dental structures not covered by the drilling template is measured using an optical three-dimensional measuring method. Then the position and orientation of the measuring element in relation to the partial region of the dental structures are determined from the generated
(Continued)

measured data of the optical measurement, wherein a virtual actual implant drilling model is created on the basis of the optical measured data using the position and orientation determined for the measuring element, and/or using the known dimensions of a drill to be used, and/or the position of a stop surface on the drilling template for the drill to be used, wherein the actual implant drilling model is compared with a planned virtual target implant drilling model from a previous implant planning with respect to its position and its orientation.

29 Claims, 1 Drawing Sheet

(58) Field of Classification Search
USPC .............................. 433/72, 75, 213, 214, 215
See application file for complete search history.

(56) References Cited

U.S. PATENT DOCUMENTS

| | | | |
|---|---|---|---|
| 2002/0102517 A1* | 8/2002 | Poirier | A61C 1/084 433/173 |
| 2005/0084144 A1* | 4/2005 | Feldman | A61C 1/084 382/128 |
| 2006/0105291 A1 | 5/2006 | Stein et al. | 433/75 |
| 2009/0092948 A1 | 4/2009 | Gantes | |
| 2009/0295795 A1* | 12/2009 | Feldman | A61C 1/084 345/419 |
| 2011/0033819 A1* | 2/2011 | Freyer | A61C 1/084 433/72 |
| 2011/0123946 A1* | 5/2011 | Bulloch | A61C 1/084 433/75 |
| 2013/0216974 A1* | 8/2013 | Schmalzle | A61C 1/082 433/75 |
| 2013/0302752 A1* | 11/2013 | Schneider | A61C 1/084 433/173 |

FOREIGN PATENT DOCUMENTS

| | | |
|---|---|---|
| EP | 1 101 451 B1 | 4/2005 |
| EP | 1 062 916 B1 | 1/2007 |
| WO | 03/060825 A2 | 7/2003 |
| WO | 2004/076106 A1 | 9/2004 |
| WO | 2006/111964 A2 | 10/2006 |
| WO | 2008/020054 A2 | 2/2008 |

OTHER PUBLICATIONS

German Office Action, dated May 15, 2012, issued in connection with German Application No. 10 2011 083 439.7, with machine translation.

International Preliminary Report on Patentability, dated Apr. 1, 2014, issued in International Patent Application No. PCT/EP2012/068900, with translation.

* cited by examiner

METHOD FOR VALIDATING A DRILLING TEMPLATE FOR PRODUCING AN IMPLANT-BORNE TOOTH REPLACEMENT

CROSS REFERENCE TO RELATED APPLICATION

The present application is a national-stage entry under 35 U.S.C. §371 of International Patent Application No. PCT/EP2012/068900, filed Sep. 26, 2012, and claims the benefit of foreign priority under 35 U.S.C. §119(a)-(d) of German Patent Application No. 10 2011 083 439.7, filed Sep. 26, 2011. The entire contents of each of the above-mentioned prior applications are incorporated herein by reference as if fully set forth herein.

TECHNICAL FIELD

The invention relates to a method for validating a drilling template for producing an implant-borne tooth replacement before performing an implant drilling, wherein the drilling template produced is placed on dental structures of a region of the jaw to be provided with the tooth replacement.

PRIOR ART

The prior art discloses a plurality of methods for producing drilling templates, wherein the alignment of the drill guides is usually validated on a plaster model having planned implant drillings or using insertion pins which are inserted into the drill guides, and a validation occurs of whether the tips of the insertion pins point to marks on a checksheet.

EP 1 062 916 B1 discloses a method for producing an individually prepared, implant-borne tooth replacement. To produce the tooth replacement, a negative impression of the jaw is produced. In the next step, a working model is produced on the basis of this negative impression. In the next step, a manipulable implant, which corresponds in its dimensions to an implant that is to be inserted, is mounted on the working model. The manipulable implants are inserted into the working model in such a way that they do not protrude. In the next step, an auxiliary element is provisionally mounted on each of the manipulable implants. In the next step, a three-dimensional measurement is performed, and then the precise location of the implants in the region of the patient's jaw is determined from the data on the geometry of the working model with the auxiliary elements arranged thereon.

One disadvantage of this method is that a working model must first be prepared of the region of the jaw for validating the drill guides of the drilling template, and in the second step, manipulable implants which correspond to the actual dimensions of the implants to be used must be inserted into the working model. When producing the working model and the manipulable implants as well as when inserting the manipulable implants in the working model, production defects and positioning errors may lead to a faulty alignment and position of the implant drillings to be performed by means of the drilling template.

The object of the present invention is therefore to provide a method for validating a drilling template with which production errors and positioning errors are to be avoided as much as possible to ensure a reliable validation of the drilling template.

DESCRIPTION OF THE INVENTION

The invention relates to a method for validating a drilling template before performing an implant drilling for an implant-borne tooth replacement, wherein the drilling template that is produced has a drill guide and is placed on dental structures of an area of the jaw which is provided with the tooth replacement, these structures being present in the region of the implant drilling to be performed. A measuring element is placed in the drill guide of the drilling template, and then the measuring element and at least one subarea of the dental structures that are not covered by the drilling template are measured using an optical three-dimensional measurement method. The position and orientation of the measuring element relative to the subarea of the dental structures is determined from the measured data generated from the optical measurement for this validation such that a virtual actual implant drilling model is created on the basis of the optical measured data using the position determined and the orientation of the measuring element, and/or the known dimensions of a drill to be used, and/or the position of a stop surface on the drilling template for the drill to be used, wherein the actual implant drilling model is compared, in regard to its position and orientation, with a planned target implant drilling model from a previous implant planning.

The drilling template may be suitable for performing one or more implant drillings with any orientations. The dental structures may be teeth, dental stumps and/or crowns in the patient's oral cavity. The dental structures of the region of the jaw to be provided with the tooth replacement may also be dental models of an impression model of this region of the jaw, for example made of plaster. The measuring element may have a fitting which may be designed for example in the form of a cylinder or may have a star-shaped cross section to be inserted with an accurate fit into the cylindrical drill guide. The measuring element must be designed so that its position and orientation can be determined unambiguously by means of the optical three-dimensional measurement method. The measuring element may have a basic geometric shape such as a cone, a cube, a sphere or a pyramid. The measuring element may also be provided with a plurality of optical markings which are arranged, for example, in the form of a triangle in relation to one another, and which permit an unambiguous determination of the position and orientation of the measuring element in relation to the visible part of the dental structures. The optical three-dimensional measurement method that is used may be, for example, the strip projection method for optical three-dimensional detection of teeth.

The position and orientation of the measuring element are determined in relation to the visible dental structures which are not covered by the drilling template. The stop surface serves as a stop for the measuring element and also for the drill to be used so that, given a knowledge of the dimensions of the drill to be used, the implant drilling to be produced can be simulated in relation to the dental structures.

By using known pattern recognition methods, the visible part of the dental structures not covered by the drilling template can be recognized in the measured data of the optical measurement for the validation as well as in measured data of a previous measurement for the implant planning and superimposed. In this way, the position and orientation of the measuring element may be determined in relation to the original measured data for the implant planning. The original measured data for the implant planning may be for example superimposed measured data of a three-dimensional optical measurement and measured data of a three-dimensional x-ray measurement.

The stop surface on the drilling template serves as a stop for insertion of the measuring element as well as for the drill to be used so that, given the knowledge of the dimensions of the drill and the position and orientation of the measuring element, the actual implant drilling model can be created of the implant drilling to be performed.

The target implant drilling model is created with the previous implant planning and constitutes an optimal implant drilling taking into account the various factors. The factors to be taken into account may include, for example, the dimensions of the implant-borne part of the tooth replacement, the course of the jaw bone and the course of the nerves and the dental roots. By comparing the actual implant drilling model with the optimal target implant drilling model, a possible deviation which would lead to a faulty implant drilling can be ascertained.

The advantage of the present method is that the drilling template can be validated directly in the patient's mouth or on an impression model even before performing the implant drilling. It is therefore possible to ascertain in the validation whether the drilling template has been placed in a skewed position on the dental structures. The causes for this might be, for example, manufacturing defects such as protruding elevations or chips between a support surface of the drilling template and the surface of the dental structures. The drilling template can then be reworked accordingly, so that when the drilling template is placed in position, the planned drill guides of the drilling template are positioned and oriented in relation to the dental structures as desired.

In addition, measurement errors which may occur in optical acquisition of the preparation field can be corrected.

An error message may advantageously be generated if, in comparison of the actual implant drilling model with the target implant drilling model, the deviation exceeds a certain tolerance range.

The error message is generated when the tolerance range, such as a deviation of the orientation of the actual implant drilling model of more than 5°, is exceeded. The user then receives a feedback message and can rework the drilling template accordingly.

The error message upon exceeding the tolerance range may be issued acoustically by means of a sound generator, or optically by means of the display device.

The actual implant drilling model and/or the target implant drilling model may advantageously be displayed on a display device in relation to the measured data of the optical measurement for the validation and/or in relation to the original measured data for the implant planning.

The actual implant drilling model may thus be displayed by means of the display device together with the original measured data for the implant planning, which may include the x-ray data and the optical measured data, as well as together with the optical measured data for the validation.

The user can thereby visually validate the position the position of the simulated actual implant drilling model with regard to critical structures from the x-ray data, such as the course of the jaw bone, the nerves or the gingiva, and/or in comparison with the target implant drilling model.

A virtual actual measuring element model can advantageously be created from the measured data of the optical measurement for the validation.

The virtual actual measuring element model is created with knowledge of the dimensions of the measuring element. Using known pattern recognition methods, the location and position of this actual measuring element model can then be determined in relation to the measured data of the optical measurement for the validation and thus in relation to the visible dental structures photographed.

The actual measuring element model created can advantageously be compared with a target measuring element model from a previous implant planning.

The target measuring element model has an optimal position and orientation of the measuring element in relation to the dental structures for a planned implant drilling. The actual measuring element model created from the optical measured data can be compared with the target measuring element model to ascertain a possible deviation which would result in a faulty implant drilling.

If the deviation in the comparison of the actual measuring element model with the target measuring element model exceeds a certain tolerance range, an error message may advantageously be generated.

The tolerance range defined depends on the dimensions of the implant-borne tooth replacement part and on the course of the jaw bone and of the nerves in the jaw of the patient. The deviation in the orientation of the actual measuring element model should not exceed a limit angle of 5°, for example. If the tolerance range is exceeded, an optical and acoustic error message is generated so that the user receives a feedback message about the faulty positioning of the drilling template. The drilling template can then be reworked accordingly to remove production-related unevenness on the support surface of the drilling template caused by production, for example.

The actual measuring element model and/or the target measuring element model may advantageously be displayed by means of a display device in relation to the measured data of the measurement for the validation and/or in relation to the measured data of the original measurement for the implant planning.

In this way, the user can visually validate the position of the simulated actual measuring element model in relation to the target measuring element model.

The dental structures of the jaw region for placement of the drilling template may advantageously be teeth, crowns and/or dental stumps in the patient's mouth.

The drilling template is therefore validated directly in the patient's oral cavity. The drilling template is placed directly on dental structures of the prepared jaw region. Next the optical three-dimensional measurement is performed in the patient's oral cavity, wherein both the measuring element and parts of the dental structures not covered by the drilling template are detected.

The dental structures of the jaw region for placement of the drilling template may advantageously be at least part of an impression model of the jaw area.

The drilling template is therefore placed on the dental structures of the impression model of the prepared jaw region. Validation of the drilling template can therefore be performed indirectly on the impression model in a central dental laboratory.

In the inserted condition, the measuring element may advantageously protrude above the drilling template.

Therefore, the measuring element can be detected better in the optical three-dimensional measurement.

The measuring element may advantageously have a fitting which is inserted into the drill guide of the drilling template.

The measuring element may have a stop surface at the connection to the fitting which lies on the stop surface of the drilling template in the inserted condition.

The fitting may advantageously be designed as a cylinder whose cylinder diameter corresponds to the diameter of the drill guide of the drilling template.

The fitting can therefore be produced easily to fit the drill that is used.

The measuring element may advantageously be introduced into the drill guide up to the stop surface of the drilling template so that the depth of insertion and thus the distance of the measuring element from the stop surface are known.

Therefore, with knowledge of the dimensions of the drill to be used, the position and orientation of the measuring element, the actual implant drilling model of the implant drilling to be performed can be simulated accurately.

BRIEF DESCRIPTION OF THE DRAWINGS

The invention will now be explained with reference to the drawings, in which.

EXEMPLARY EMBODIMENT

Figure 1:
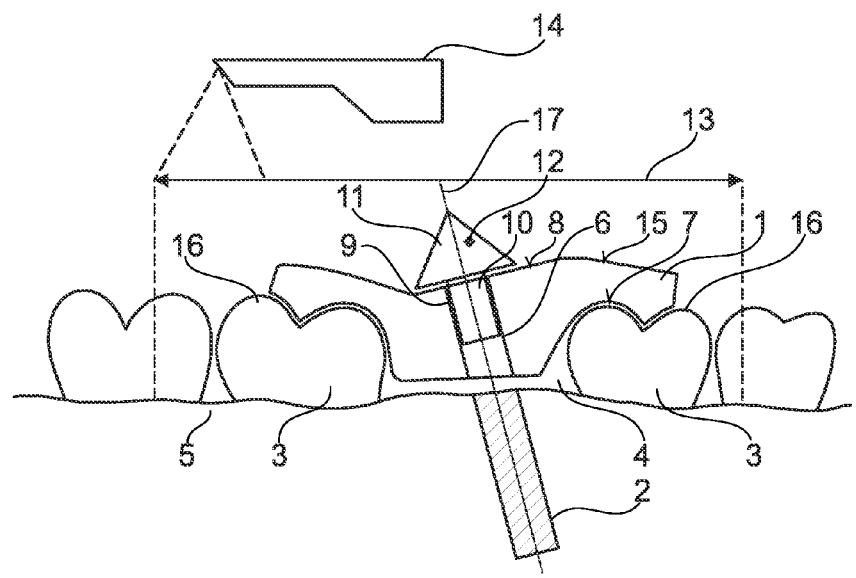
FIG. 1 shows a diagram to illustrate a first step in the method, wherein a drilling template is placed on dental structures for validation.
Figure 2:
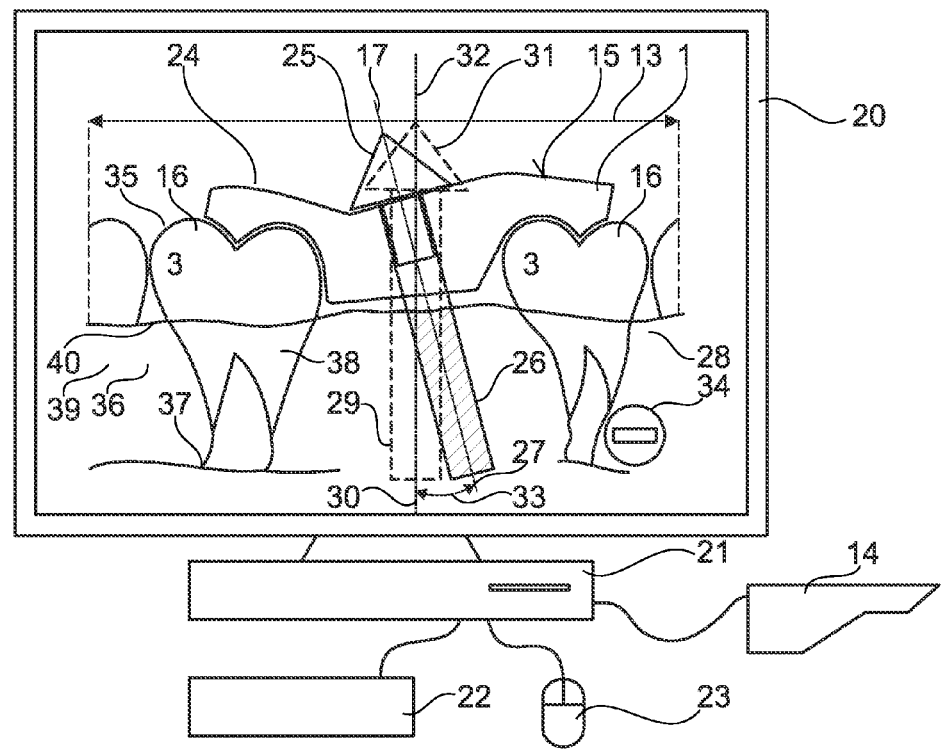
FIG. 2 shows a diagram to illustrate an additional step of the method, wherein the three-dimensional optical measured data generated are displayed by means of a display device.

To illustrate the present method, FIG. 1 shows a drilling template 1 which is placed on dental structures 3 for validation before performing a planned implant drilling 2. The dental structures 3 are the teeth adjacent to a preparation region 4 or parts of an impression model of a jaw region 5 to be provided with an implant-borne tooth replacement. The drilling template 1 has a cylindrical drill guide 6, a support surface 7 and a stop surface 8. A cylindrical fitting 9 is inserted into the drill guide 6, this dental fitting having the same diameter as the drill guide 6. A conical measuring element 11 is situated at the upper end of the fitting 9. The measuring element 11 may also have one or more basic geometric shapes such as a rectangle, a sphere or a pyramid. The measuring element 11 is provided with optical markings 12. However, the measuring element 11 may also be designed without optical markings so that the position and orientation of the measuring element 11 can be derived from the shape. The jaw region 5 is measured by means of an optical three-dimensional method using a corresponding measuring device 14 in a measuring range 13, which is indicated by the dashed lines and the horizontal arrow. The measuring device 14 may be a dental handpiece which operates according to the so-called strip projection method for detecting three-dimensional objects. In the optical three-dimensional measurement by means of the measuring device 14, three-dimensional measured data are generated, comprising both the surface 15 of the drilling template and at least a portion 16 of the dental structures 3 which are not covered by the drilling template 1. The precise position and orientation of the measuring element 11 along the longitudinal axis 17 can be determined on the basis of the optical measuring data generated in order to determine the position and orientation of the implant drilling 2 to be produced therefrom. FIG. 2 shows another step in the present method, where the measured data generated in the optical three-dimensional measurement for the validation of the measuring range 13 from FIG. 1 is displayed graphically by means of a display device 20 such as a monitor. The measured data of the measuring range 13 includes the surface 15 of the drilling template 1 and parts 16 of the dental structures 3 which are not covered by the drilling template 1. The display device 20 is connected to a computer 21 which processes measured data generated by the measuring device 14. Input devices such as a keyboard 22 and a mouse 23 are connected to the computer 21. Using known pattern recognition methods or manual selection by means of the input devices 22, 23, a virtual actual measuring element model 25 of measuring element 11 is determined from the optical three-dimensional measured data 24. The stop surface 8 from FIG. 1 serves as a stop for the measuring element 11 as well as being a stop for the drill to be used. Therefore, by using the known dimensions of the drill to be used, a virtual actual implant drilling model 26 can be determined from the position and orientation of the virtual actual measuring element model 25. The virtual actual implant drilling model 26 may also be simulated without generating a virtual actual measuring element model 25, in which case the actual implant drilling model 26 is calculated directly from the positions of the markings 12 or from the position and orientation of the measuring element 11. The longitudinal axis of the actual measuring element model 17 matches the longitudinal axis 27 of the actual implant drilling model 26. A target implantation drilling model 29 is created in a previous implant planning, taking into account the course of the jaw bone 28 and the dimensions of the implant-borne tooth replacement (not shown here), this target implant drilling model being shown with broken lines and having a longitudinal axis 30. A virtual target measuring element model 31 having a longitudinal axis 32 can also be generated in implant planning. By means of the computer 21, a comparison is made between the actual implant drilling model 26 and the target implant drilling model 29 such that a deviation such as angle 33 between the longitudinal axis 27 and the longitudinal axis 30 is defined. If the angle 33 exceeds a certain tolerance range such as an angle of 5°, for example, an error message 34 lights up, represented as a graphic symbol. The user can thereby ascertain that the deviation is outside of the tolerance range and that reworking of the validated drilling template 1 is necessary. A reason for the deviation might be unevenness on the support surface 7 due to fabrication, for example. This unevenness can be removed by reworking. Tilting when placing the drilling template 1 on the dental structures 3 may also cause a deviation between the actual implant drilling model and the target implant drilling model. In an additional and/or alternative process step, the actual measuring element model 25 may be compared with the target measuring element model 31 and validated for whether the deviation is within a certain tolerance range. If this tolerance range is exceeded, the error message 34 is generated.

The visible part 16 of the dental structures 3 not covered by the drilling template 1 is detected by means of known pattern recognition methods both in the three-dimensional optical measured data 24 for the validation and in the three-dimensional optical measured data 35 of a previous measurement for the implant planning, and these are superimposed. The original optical measured data is linked to three-dimensional x-ray data 36 of an x-ray measurement for the implant planning. Therefore the position and orientation of the actual measuring element model 25 or of the actual implant drilling model 26 can be determined in relation to the original optical measured data 35 and to the x-ray data 36 for the implant planning. The original x-ray data 36 for the implant planning has critical structures such as nerves 37, dental roots 38, the jaw bone 39 or the course of the gingiva 40. The user can therefore visually validate the position of the simulated actual implant drilling model 26 with respect to these critical structures and correct them by adjusting the drilling template accordingly, if necessary.

REFERENCE NUMERALS

1 Drilling template
2 Implant drilling

3 Dental structures
4 Preparation region
5 Jaw region
6 Drill guide
7 Support surface
8 Stop surface
9 Fitting
11 Measuring element
12 Optical marking
13 Measuring range
14 Measuring device
15 Surface
16 Part of the dental structures
17 Longitudinal axis
20 Display device
21 Computer
22 Keyboard
23 Mouse
24 Three-dimensional measured data
25 Actual measuring element model
26 Actual implant drilling model
27 Longitudinal axis
28 Jaw bone
29 Target implant drilling model
30 Longitudinal axis
31 Target measuring element model
32 Longitudinal axis
33 Angle
34 Error message
35 Original three-dimensional optical measured data
36 Three-dimensional x-ray data
37 Nerves
38 Dental roots
39 Jaw bone
40 Gingiva The inventon claimed is:

1. A method for validating a drilling template before performing an implant drilling for an implant-borne tooth replacement, wherein the drilling template comprises a drill guide and is placed on dental structures of a jaw area that is to be provided with the tooth replacement and which are present in the region of the implant drilling to be performed, the method comprising:
   inserting a measuring element into the drill guide of the drilling template,
   measuring the measuring element and at least one partial region of the dental structures not covered by the drilling template using an optical three-dimensional measuring method,
   determining a position and orientation of the measuring element in relation to the partial region of the dental structures from generated measured data of the optical measurement,
   creating a virtual actual implant drilling model on the basis of the optical measured data using the position and orientation determined for the measuring element and/or using the known dimensions of a drill to be used and/or the position of a stop surface on the drilling template for the drill to be used,
   comparing the actual implant drilling model with a planned virtual target implant drilling model from a previous implant planning with respect to its position and its orientation, and
   introducing the measuring element into the drill guide up to the stop surface, so that the depth of insertion and thus a spacing of the measuring element from the stop surface are known, wherein the measuring element has a fitting which is inserted into the drill guide of the drilling template, and wherein the measuring element is designed so that its position and orientation can be determined unambiguously by the optical three-dimensional measuring method.

2. The method according to claim 1, further comprising generating an error message when a deviation in comparison of the actual implant drilling model with the target implant drilling model exceeds a certain tolerance range.

3. The method according to claim 1, further comprising displaying the actual implant drilling model and/or the target implant drilling model by a display device in relation to the measured data of the optical measurement for the validation and/or in relation to the original measured data for the implant planning.

4. The method according to claim 1, further comprising generating a virtual actual measuring element model from the measured data of the optical measurement for the validation.

5. The method according to claim 4, further comprising comparing the actual measuring element model generated with a target measuring element model from a previous implant planning.

6. The method according to claim 5, further comprising generating an error message when the deviation in comparison of the actual measuring element model with the target measuring element model exceeds a certain tolerance range.

7. The method according to claim 5, further comprising displaying the actual measuring element model and/or the target measuring element model by a display device in relation to the measured data of the measurement for the validation and/or in relation to the original measured data for the implant planning.

8. The method according to one of claims 1 to 7, wherein the dental structures of the jaw area are represented by an impression model of the jaw area.

9. The method according to claim 1, wherein the dental structures of the jaw region for placement of the drilling template are teeth, crowns and/or stumps of teeth in the patient's oral cavity.

10. The method according to claim 1, wherein the measuring element protrudes above the drilling template in the inserted condition.

11. The method according to claim 1, wherein the fitting is designed as a cylinder whose diameter corresponds to the diameter of the drill guide of the drilling template.

12. A method for validating a drilling template, the method comprising:
   placing the drilling template on dental structures of a jaw area that are present in a region of an implant drilling to be performed, the drilling template comprising a drill guide;
   inserting a measuring element into the drill guide of the drilling template;
   measuring the measuring element and at least one partial region of dental structures not covered by the drilling template using a measuring method to generate measured data;
   determining a position and an orientation of the measuring element in relation to the at least one partial region of the dental structures from the generated measured data;
   creating a virtual implant drilling model on the basis of the generated measured data; and
   comparing the virtual implant drilling model with a planned target implant drilling model from a previous implant planning with respect to a position and an orientation of the virtual implant drilling model, to validate the position and the orientation of the virtual implant drilling model with respect to the planned target implant drilling model.

13. The method according to claim 12, wherein the measuring element is inserted into the drill guide up to a stop surface of the drilling template, such that a depth of insertion and a spacing of the measuring element from the stop surface are known.

14. The method according to claim 12, wherein the measuring element has a fitting that is also inserted into the drill guide of the drilling template.

15. The method according to claim 14, wherein the fitting is designed as a cylinder whose diameter corresponds to a diameter of the drill guide of the drilling template.

16. The method according to claim 12, wherein the measuring element protrudes above the drilling template in the inserted condition.

17. The method according to claim 12, wherein the dental structures of the jaw area for placement of the drilling template are at least one of teeth, crowns, and stumps of teeth in an oral cavity of a patient.

18. The method according to claim 12, wherein the measuring method is an optical three-dimensional measuring method.

19. The method according to claim 12, wherein the virtual implant drilling model is created using at least one of (i) the position and the orientation determined for the measuring element, (ii) known dimensions of a drill to be used with the drilling template, and (iii) a position of a stop surface on the drilling template.

20. The method according to claim 12, wherein the method is conducted before performing the implant drilling.

21. The method according to claim 12, further comprising adjusting the drilling template if, during the comparing step, a comparison of the virtual implant drilling model with the planned target implant drilling model exceeds a certain tolerance range.

22. The method according to claim 12, further comprising generating an error message when, during the comparing step, a deviation in a comparison of the virtual implant drilling model with the planned target implant drilling model exceeds a certain tolerance range.

23. The method according to claim 22, further comprising adjusting the drilling template if the comparison of the virtual implant drilling model with the planned target implant drilling model exceeds the certain tolerance range.

24. The method according to claim 12, further comprising displaying at least one of the virtual implant drilling model and the planned target implant drilling model with a display device, in relation to at least one of (i) the generated measured data and (ii) original measured data from the previous implant planning.

25. The method according to claim 12, further comprising generating a virtual measuring element model from the generated measured data.

26. The method according to claim 25, further comprising comparing the virtual measuring element model with a target measuring element model from a previous implant planning.

27. The method according to claim 26, further comprising generating an error message when, during the comparing step, a deviation in a comparison of the virtual measuring element model with the target measuring element model exceeds a certain tolerance range.

28. The method according to claim 26, further comprising displaying at least one of the virtual measuring element model and the target measuring element model with a display device, in relation to at least one of (i) the generated measured data and (ii) original measured data from the previous implant planning.

29. The method according to one of claims 12 to 28, wherein the dental structures of the jaw area are represented by an impression model of the jaw area.

* * * * *